United States Patent
Harris et al.

(10) Patent No.: US 6,638,928 B1
(45) Date of Patent: Oct. 28, 2003

(54) TREATMENT OF IRRITABLE BOWEL SYNDROME AND NONULCER DYSPEPSIA WITH SUBSTITUTED 2,3-BENZODIAZEPINES

(75) Inventors: Herbert W. Harris, Merion, PA (US); Robert F. Kucharik, Glenmoore, PA (US)

(73) Assignee: Vela Pharmaceuticals, Inc., Lawrenceville, NJ (US)

(*) Notice: Subject to any disclaimer, the term of this patent is extended or adjusted under 35 U.S.C. 154(b) by 0 days.

(21) Appl. No.: 10/309,526

(22) Filed: Dec. 3, 2002

(51) Int. Cl.$^7$ ............................................. A61K 31/551
(52) U.S. Cl. ................................................ 514/221
(58) Field of Search ........................................ 514/221

(56) References Cited

U.S. PATENT DOCUMENTS

| | | | |
|---|---|---|---|
| 3,736,315 A | 5/1973 | Kórósi et al. | 540/567 |
| 4,322,346 A | 3/1982 | Kórósi et al. | 540/567 |
| 4,423,044 A | 12/1983 | Kórósi et al. | 514/221 |
| 4,614,740 A | 9/1986 | Láng et al. | 514/221 |
| 4,835,152 A | 5/1989 | Kórósi et al. | 514/220 |
| 4,840,948 A | 6/1989 | Láng et al. | 514/221 |
| 5,204,343 A | 4/1993 | Andrási et al. | 514/221 |
| 5,288,863 A | 2/1994 | Somogyi et al. | 540/567 |
| 5,459,137 A | 10/1995 | Andrási et al. | 514/220 |
| 5,519,019 A | 5/1996 | Andrási et al. | 514/220 |
| 5,521,174 A | 5/1996 | Andrási et al. | 514/220 |
| 5,639,751 A | 6/1997 | Andrási et al. | 514/220 |
| 5,891,871 A | 4/1999 | Xia et al. | 514/219 |
| 6,075,018 A | 6/2000 | Vágó et al. | 514/221 |
| 6,080,736 A | 6/2000 | Landry et al. | 514/221 |

FOREIGN PATENT DOCUMENTS

| | | |
|---|---|---|
| EP | 0 492 485 A1 | 7/1992 |
| HU | 178516 | 3/1983 |
| WO | WO 92/11262 | 7/1992 |

OTHER PUBLICATIONS

F. Gatta et al., "Derivatives of 2,3–Benzodiazepine (*)", Il Farmaco—Ed. Sc.—vol. 40—fasc. 12, pp. 942–955 (1983).

R. Sladká et al., "A Placebo–controlled Clinical Trial with Tofizopam * in the Treatment of Anxiety Neurosis" Division of Psychiatry, District Institutes of National Health, Prague, 2 and 4; Psychiatric Department and Psychiatric Research Unity, Medical Scholl of Charles University, Prague, Czechoslovakia, pp. 176–180 (1979).

Edit J. Horváth et al., "Anxiolytic 2,3–benzodiazepines, their Specific Binding to the Basal Ganglia", Progress in Neurobiology vol. 60 (2000), pp. 309–342.

E. Tomori et al., "Investigation of the Metabolites of Tofizopam in Man and Animals by Gas–Liquid Chromatography–Mass Spectrometry", Journal of Chromatography, 241 (1982), pp. 89–99.

Eva Tomori et al., "Investigation of Metabolites of Tofizopam in Man and Animals", Polish Journal of Pharmacology and Pharmacy, 1984, 36, pp. 423–430., PL ISSN 0301–0214.

Sharon Pellow et al., "The Effects of Tofisopam, a 3,4–Benzodiazepine, in Animal Models of Anxiety, Sedation, and Convulsions", Drug Development Research 7, pp. 61–73 (1986).

A. Bond et al., "A Comparison of the Psychotropic Profiles of Tofisopam and Diazepam", Fur J Clin Pharmacol (1982) 22, pp. 137–142.

J. Kanto et al., "Tofizopam: A Benzodiazepine Derivative Without Sedative Effect", International Journal of Clinical Pharmacology, Therapy and Toxicology, vol. 20 No. 7—1982, pp. 309–312.

T. Mennini et al., "Brain Levels of Tofizopam in the Rat and Relationship with Benzodiazepine Receptors", Naunyn–Schmiedeberg's Arch Pharmacol (1982) 321, pp. 112–115.

K. Maier et al., "The Effect of Tofisopam on Psychic Performance in Persons with More than Average Anxiety: A Controlled Experimental Trial", Current Therapeutic Research, vol. 35, No. 4, Apr. 1984, pp. 541–548.

Chihiro Ito, Behavioral Pharmacological Study of the Structure–Activity Relationship of Benzodiazepine Derivatives—with Particular Reference to the Activity of 2,3–Benzodiazepine–, (1981) 39(3), pp. 369–384 (Japanese), pp. 1–30 (English Translation).

Giovambattista De Sarro et al., "GYKI 52466 and Related 2,3–Benzodiazepines as Anticonvulsant Agents in DBA/2 Mice", European Journal of Pharmacology 294 (1995), pp. 411–422.

T. Seppälä, "Tofisopam, A Novel 3,4–Benzodiazepine: Multiple–Dose Effects on Psychomotor Skills and Memory. Comparison with Diazepam and Interactions with Ethanol", Psychopharmacology 69, (1980), pp. 209–218.

(List continued on next page.)

Primary Examiner—Phyllis G. Spivack
(74) Attorney, Agent, or Firm—Drinker Biddle & Reath lLLP

(57) ABSTRACT

Compounds according to formula I:

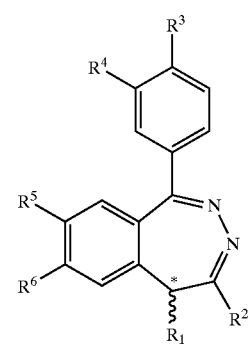

are disclosed wherein $R^1$, $R^2$, $R^3$, $R^4$, $R^5$ and $R^6$ as defined herein, are administered for irritable bowel syndrome and nonulcer dyspepsia.

13 Claims, No Drawings

OTHER PUBLICATIONS

Veijo Saano et al., "Tofizopam Modulates the Affinity of Benzodiazepine Receptors in the Rat Brain", Pharmacology Biochemistry & Behavior, vol. 17, (1982), pp. 367–369.

Sharon Pellow et al., "The Effects of Tofisopam, a 3,4–Benzodiazepine, in Animal Models of Anxiety, Sedation, and Convulsions", Drug Development Research 7 (1986), pp. 61–73.

A. Pakkanen et al., "Comparative Study of the Clinical Effects of Tofizopam, Nitrazepam and Placebo as Oral Premedication", British Journal of Anaesthesics, pp. 1009–1012 (1980).

V. Saano et al., "Tofizopam Enhances the Action of Diazepam Against Tremor and Convulsions", Medical Biology 61: (1983), pp. 49–53.

V. Saano et al., "Tofizopam Selectively Increases the Action of Anticonvulsants", Medical Biology, 64 (1986), pp. 201–206.

István Tarnawa et al., "Structure–Activity Relationships of 2,3–Benzodiazepine Compounds with Glutamate Antagonistic Action", Bioorganic & Medical Chemistry Letters, vol. 3, No. 1, (1993), pp. 99–104.

K. Yamaguchi et al., "Tofisopam, A New 2,3–Benzodiazepine. Inhibition of Changes Induced by Stress Loading and Hypothalamic Stimulation", Can. J. Physiol Pharmaco, vol. 61, (1983), pp. 619–625.

Szegó Judit et al., "Selected Passages From the Clinical–Pharmacological and Clinical Trials of Grandaxin®, " Acta Pharmaceutica Hungarica vol. 63, (1993), pp. 91–98 (Hungarian). pp. 1–10 (English Translation Provided).

L. Petócz et al., The Main Pharmacological Characteristics of Grandaxin (Tofizopam, Egyt–341), Hungarian Medical Journal, vol. 23, No. 4, (1975), pp. 134–138.

Petócz Luijza, "The Pharmacological Effects of Tofizopam (Grandaxin)®", Acta Pharmaceutica Hungarica, vol. 63, (1993), pp. 79–82 (Hungarian. pp. 1–4 (English Translation Provided).

Study of efficacy and safety of Grandaxin tablets for unidentified complaints with digestive system disease. Asano Sadhiro, Orita Yuichi, Kuga Masafumi and Amamor Masanori. Journal of New Remedies & Clinics, 1993, vol. 42, No. 12, pp. 2551–2556. English translation provided.

Clinical Evaluation of Tofisopam (Grandaxin) on Gastro–intestinal Various Unidentified Complaints. Aoyagi Toshio, Kubo Akiyoshi, Sano Masaaki, Kashiwazaki Kazuo, Kojima Toshiya, Nishizato Yoshinori, Koizumi Kazumasa, Yoshioka Masahiro and Miyake Shozo. Japanese Pharmacology & Therapeutics, 1992, vol. 20, No. 2, pp. 657–667. English translation provided.

From actual practice of diagnosis and treatment. Clinical effect of tofisopam (Grandaxin) on unidentified complaints of digestive system. Kitano Atsuo, Okabe Hiroshi, Nakamura Shiro, Obata Akishige, Oshitani Nobuhide, Hioki Masato, Matsumoto Takayuki, Okawa Kiyotaka and Kobaysashi Junzo. Journal of New Remedies & Clinics, 1988, vol. 37, No. 9, pp. 1735–1739. English translation provided.

Effect of Tofisopam (Grandaxin) on irritable colon and cardiac neurosis. Hanajima H. Journal: Yakuri to chiryo. (Japanese pharmacology and therapeutics), 1987, vol. 15. No. 15, pp. 307–217. English translation provided.

TREATMENT OF IRRITABLE BOWEL SYNDROME AND NONULCER DYSPEPSIA WITH SUBSTITUTED 2,3-BENZODIAZEPINES

FIELD OF THE INVENTION

The present invention relates to methods of treatment for irritable bowel syndrome and for nonulcer dyspepsia.

BACKGROUND OF THE INVENTION 2,3-Benzodiazepines

Certain 2,3-benzodiazepines have been explored extensively for their potent CNS modulating activity. Compounds such as tofisopam (Grandaxin®)(structure shown below, with the atom numbering system indicated), girisopam, and norisopam have demonstrated substantial anxiolytic and antipsychotic activity.

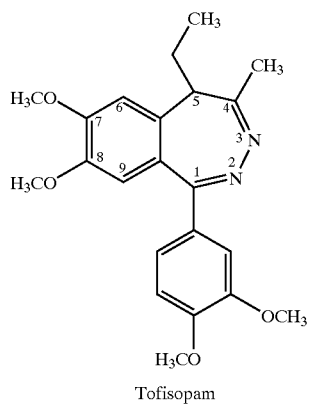

Tofisopam

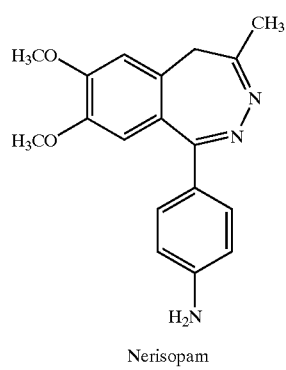

Nerisopam

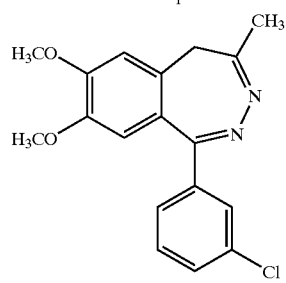

Girisopam

Tofisopam has been shown in humans to have an activity profile that is significantly different from that of widely used 1,4-benzodiazepine (BZ) anxiolytics such as diazepam (Valium®) and chlordiazepepoxide (Librium®). The 1,4-benzodiazepines, in addition to having sedative-hypnotic activity, also possess muscle relaxant and anticonvulsant properties which, though therapeutically useful in some disease states, are nonetheless potentially untoward side effects. Thus the 1,4-benzodiazepines, though safe when administered alone, may be dangerous in combination with other CNS drugs, including alcohol.

Tofisopam, in contrast, is a non-sedative anxiolytic that has no appreciable sedative, muscle relaxant or anticonvulsant properties See Horvath el al., *Progress in Neurobiology,* 60 (2000), 309–342, the entire disclosure of which is incorporated herein by reference. In clinical studies, tofisopam improved rather than impaired psychomotor performance and showed no interaction with ethanol (Id.). These observations comport with data that show that tofisopam does not interact with central BZ receptors and binds only weakly to peripheral BZ receptors.

Other 2,3-benzodiazepines that are structurally similar to tofisopam have been investigated and shown to have varying activity profiles. For example, GYKI-52466 and GYKI-53655 (structures shown below) act as noncompetitive glutamate antagonists at the AMPA (α-amino-3-hydroxy-5-methyl-4-isoxazolepropionic acid) site, and have demonstrated neuroprotective, muscle relaxant and anticonvulsant activity (Id.). Another group of 2,3-benzodiazepines that have been investigated are represented by the compound GYKI-52895, and show activity as selective dopamine uptake inhibitors with potential use in antidepressant and anti-Parkinsonism therapy.

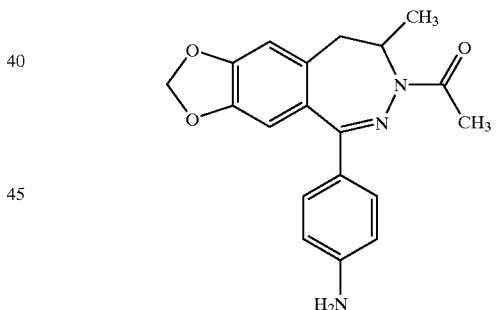

GKY-53655

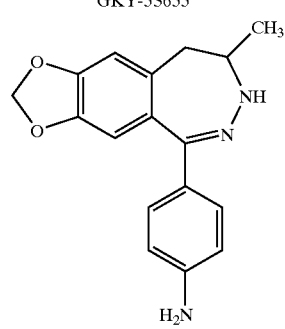

GKY-52895

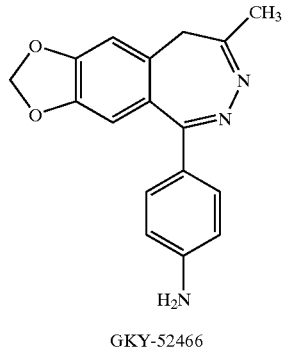

GKY-52466

Tofisopam is a racemic mixture of (R)- and (S)-enantiomers. This is due to the asymmetric carbon, i.e., a carbon with four different groups attached, at the 5-position of the benzodiazepine ring.

The structure and conformational properties of tofisopam have been determined by NMR, CD and x-ray crystallography See Visy el al., *Chirality* 1:271–275 (1989), the entire disclosure of which is incorporated herein by reference. The 2,3-diazepine ring exists as two different conformers. The major conformers, (+)R and (−)S have the 5-ethyl group in a quasi-equatorial position. In the minor conformers, (−)R and (+)S, the 5-ethyl group is positioned quasi-axially. Thus, racemic tofisopam may exist as four molecular species, i.e., two enantiomers, each of which exists in two conformations. The sign of the optical rotation is reversed upon inversion of the diazepine ring from one conformer to the other. In crystal form, tofisopam exists only as the major conformations, with dextrorotatory tofisopam being of the (R) absolute configuration. See Toth et al., *J Heterocyclic Chem.*, 20:709–713 (1983); Fogassy et al., *Bioorganic Heterocycles*, Van der Plas, H. C., Ötvös, L, Simongi, M., eds. Budapest Amsterdam: Akademia; Kiado-Elsevier, 229:233 (1984), the entire disclosures of which are incorporated herein by reference.

Differential binding of these two conformations of tofisopam is reported in binding studies with human albumin See Simongi et al. *Biochem. Pharm.*, 32(12), 1917–1920, 1983, the entire disclosure of which is incorporated herein by reference. The two conformers have also been reported as existing in equilibrium See Zsila et al., *Journal of Liquid Chromatography & Related Technologies*, 22(5), 713–719, 1999; and references therein, the entire disclosures of which are incorporated herein by reference.

The optically pure (R)-enantiomer of tofisopam (R)-1-(3,4-dimethoxyphenyl)-4-methyl-5-ethyl-7,8-dimethoxy-5H-2,3-benzodiazepine) has been isolated and shown to possess the nonsedative anxiolytic activity of the racemic mixture. See U.S. Pat. No. 6,080,736; the entire disclosure of which is incorporated herein by reference.

Metabolism of Tofisopam

Tofisopam is metabolized in human, rat, dog, monkey and rabbit to one or more of six major metabolites, depending on the host species:

Metabolism of tofisopam
Tofisopam is metabolized in human, rat, dog, monkey and rabbit to one or more of six major metabolites, depending on the host species:

| Compound # | Compound Name |
|---|---|
| 1 | 1-(3,4-dimethoxyphenyl)-4-methyl-5-ethyl-7-hydroxy-8-methoxy-5H-2,3-benzodiazepine |
| 2 | 1-(3,4-dimethoxyphenyl)4-methyl-5-ethyl-7-methoxy-8 hydroxy-5H-2,3-benzodiazepine |
| 3 | 1-(3-methoxy-4-hydroxyphenyl)-4-methyl-5-ethyl-7,8-dimethoxy-5H-2,3-benzodiazepine |
| 4 | 1-(3-hydroxy-4-methoxyphenyl)-4-methyl-5-ethyl-7,8-dimethoxy-5H-2,3-benzodiazepine |
| 5 | 1-(3-methoxy-4-hydroxyphenyl)-4-methyl-5-ethyl-7-hydroxy-8-methoxy-5H-2,3-benzodiazepine |
| 6 | 1-(3-hydroxy-4-methoxyphenyl)-4-methyl-5-ethyl-7-hydroxy-8-methoxy-5H-2,3-benzodiazepine |

See Tomori et al., *Journal of Chromatography*, 241 (1982), p. 89–99.

Of the compounds named above, Compounds 1, 3 and 5 have been identified as metabolites in humans. These compounds have been synthesized and tested in certain pharmacological assays. See C. Ito, "Behavioral Pharmacological Study on the Structure Activity Relationship of Benzodiazepine Derivatives: With Particular Reference to the Activity of 2,3-Benzodiazepine," *J. Tokyo Med. College*, 39:369–384 (1981).

In an assay of inhibition of aggression in mice, Compound 1 and 3 showed 0% inhibition of aggression and Compound 5 showed a 28.6% inhibition of aggression. In an assay of muricide (mouse killing behavior) in rats, Compound 3 exhibited 0% inhibition of muricide while Compounds 1 and 5 each exhibited a 20% inhibition of muricide. In assays testing for anti-noradrenergic effects, Compound 1 exhibited no effect, while Compounds 3 and 5 demonstrated measurable activity. See Ito, Id.

Compounds 1, 3, 5 and 6 are also disclosed in U.S. Pat. No. 4,322,346, the entire disclosure of which is incorporated herein by reference. Compound 3 is reported therein to demonstrate narcosis-potentiating activity in mice.

Irritable Bowel Syndrome

Irritable bowel syndrome (IBS) is a common disorder that has a pronounced effect on the quality of life and that accounts for a large proportion of healthcare costs. IBS is defined on the basis of the recently modified Rome criteria as (A) the presence for at least 12 weeks (not necessarily consecutive) in the preceding 12 months of abdominal discomfort or pain that cannot be explained by structural or biochemical abnormalities, and (B) at least two of the following three (1) pain relieved with defecation; (2) pain, when the onset thereof is associated with a change in the frequency of bowel movements (diarrhea or constipation); and pain, when the onset thereof is associated with a change in the form of the stool (lose, watery, or pellet-like). IBS may be divided into four subcategories according to whether the predominant symptom is abdominal pain, diarrhea, constipation, or constipation alternating with diarrhea.

Approximately 15 percent of U.S. adults report symptoms that are consistent with the diagnosis of the IBS; the disease affects three times as many women as men. Whether this difference reflects a true predominance of the disorder among women or merely the fact women are more likely to seek medical care has not been determined. IBS is the most common diagnosis made by gastroenterologists in the United States and accounts for 12 percent of visits to primary care providers. It is estimated that only 25 percent of persons with this condition seek medical care for it, and studies suggest that those who seek care are more likely to have behavioral and psychiatric problems than are those who do not seek care. In addition, patients with a diagnosis of IBS are at increased risk for other, non-gastrointestinal functional disorders such as fibromyalgia and interstitial cystitis. The irritable bowel syndrome accounts for an estimate $8 billion in direct medical costs and $25 billion in indirect costs annually in the United States.

Converging evidence supports the concept that IBS results from altered regulation of gastrointestinal motility and epithelial function, as well as altered perception of visceral events. See Mayer et al., *Digestive Diseases,* 2001, 19:212–218, the entire disclosure of which is incorporated herein by reference.

Altered bowel motility, visceral hypersensitivity, psychosocial factors, an imbalance in neurotransmitters, and infection have all been proposed as playing a part in the development of the irritable bowel syndrome. See B. Horwitz et al., *The New England Journal of Medecine,* 344:24, 2001, the entire disclosure of which is incorporated herein by reference.

Nonulcer Dyspepsia

Nonulcer dyspepsia (NUD) has been defined as chronic or recurrent upper abdominal pain or discomfort for a period of more than three months' duration, with symptoms present for more than 25 percent of the time, in the absence of another organic cause. See Fisher R S, Parkman H P, "Management of nonulcer dyspepsia," *New Engl J Med* 1998; 339: 1376–1381, the entire disclosure of which is incorporated herein by reference. A simpler definition is that offered by Locke: "persistent or recurrent upper abdominal pain or discomfort with no structural or biochemical explanation for the patient's symptoms." See Locke GR, "Non-ulcer dyspepsia: what it is and what it is not," *Mayo Clin Proc* 1999;74:1011–15, the entire disclosure of which is incorporated herein by reference NUD may include bloating, nausea, early satiety, eructation and heartburn. It is a symptom complex rather than a specific condition. An organic cause is found in only 40 percent of patients with dyspepsia. The most common causes are gastroduodenal ulcer, GERD, gastroparesis, and gastric cancer. Other causes include cholelithiasis or choledocolithiasis, pancreatitis, carbohydrate malabsorption, intestinal parasites, NSAID or other medication injury, diabetes, thyroid disorders or connective tissue disorders, ischemic bowel, and abdominal cancer. The 60 percent of patients without an organic cause are considered to have "nonulcer dyspepsia," and fall into a continuum of functional gastrointestinal disorders, including irritable bowel syndrome, functional heartburn, and noncardiac chest pain. See Freidman L S., *"Helicobacter pylori* and Nonulcer Dyspepsia," *New Engl J Med* 1998; 339: 1928–30, the entire disclosure of which is incorporated herein by reference.

NUD has many similarities to IBS. NUD and IBS are usually differentiated by whether the abdominal pain is associated with abnormal bowel habits. If the association is present, the condition is considered to be IBS rather than NUD.

Like IBS, the cause of NUD is not well understood. NUD is most likely caused by an alteration in the perception of sensations arising from the gut. Other possible causes of NUD have been investigated, including Helicobacter pylori infection (a bacterial infection in the stomach that is associated with ulcer disease), and an alteration in the function of the stomach, resulting in a delayed emptying of the stomach contents. About 25–50% of patients with NUD have slowed emptying from the stomach which may, in part, explain the increased symptoms after meals.

New agents are needed which are useful in the treatment of IBS and NUD. In particular, agents are needed that are appropriate for chronic long-term use in treatment and prevention these chronic disorders.

SUMMARY OF THE INVENTION

In one embodiment of the invention a method of treating or preventing IBS or NUD is provided, comprising administering to an individual in need of such treatment an effective amount of at least one compound according to formula I:

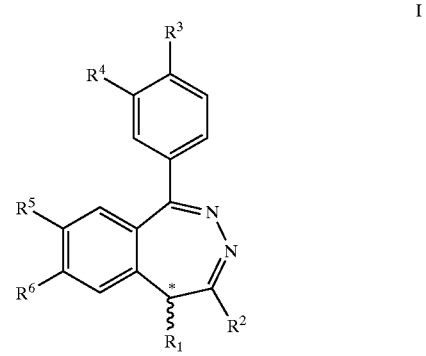

wherein:

R$^1$ is —(C$_1$–C$_7$)hydrocarbyl or —(C$_2$–C$_6$)heteroalkyl;

R$^2$ is —H or —(C$_1$–C$_7$)hydrocarbyl; wherein R$^1$ and R$^2$ may combine to form a carbocyclic or heterocyclic 5- or 6-membered ring; and one of R$^3$, R$^4$, R$^5$ or R$^6$ (hereinafter, collectively "phenyl ring substituents") is —OH, and the remaining phenyl ring substituents are independently selected from the group consisting of —(C$_1$–C$_7$)hydrocarbyl, —CF$_3$, —O(C$_1$–C$_7$)hydrocarbyl, —O-acyl, —NH$_2$, —NH(C$_1$–C$_6$)alkyl, —N((C$_1$–C$_6$)alkyl)$_2$, —NH-acyl and halogen, wherein R$^5$ and R$^6$ may combine to form a 5, 6- or 7-membered heterocyclic ring; and wherein the carbon-carbon single bond designated by ⁓ indicates that the absolute conformation about C* may be either (R) or (S);

or a pharmaceutically acceptable salt thereof.

According to a first sub-embodiment of a compound of formula I, one of R$^3$ or R$^4$ is —OH, and the other phenyl ring substituents are independently selected from the group consisting of —(C$_1$–C$_7$)hydrocarbyl, —CF$_3$, —O(C$_1$–C$_7$) hydrocarbyl, —O-acyl, —NH$_2$, —NH(C$_1$–C$_6$)alkyl, —N((C$_1$–C$_6$)alkyl)$_2$, —NH-acyl and halogen.

According to a second sub-embodiment of a compound of formula I, one of R$^3$ or R$^4$ is —OH, one or two of the other phenyl ring substituents is —OCH$_3$, and the other phenyl ring substituent(s) are independently selected from the group consisting of —(C$_1$–C$_7$)hydrocarbyl, —CF$_3$, —O(C$_1$–C$_7$) hydrocarbyl, —O-acyl, —NH$_2$, —NH(C$_1$–C$_6$)alkyl, —N((C$_1$–C$_6$)alkyl)$_2$, —NH-acyl and halogen.

According to a third sub-embodiment of a compound of formula I, one phenyl ring substituent is —OH, and the other phenyl ring substituents are independently selected from —O(C$_1$–C$_7$)hydrocarbyl.

According to a fourth sub-embodiment of a compound of formula I, one phenyl ring substituent is —OH, and the other phenyl ring substituents are independently selected from —O($C_1$–$C_7$)alkyl.

According to a fifth sub-embodiment of a compound of formula I, one phenyl ring substituent is —OH, and the other phenyl ring substituents are —$OCH_3$.

Preferably, the phenyl ring substituent which is —OH in the third, fourth and fifth sub-embodiments, is $R^3$ or $R^4$.

In some embodiments of the invention, $R^1$ and $R^2$ are independently selected from —($C_1$–$C_7$)alkyl, preferably, —($C_1$–$C_3$)alkyl. In a preferred sub-embodiments $R^1$ is —$CH_2CH_3$ and $R^2$ is —$CH_3$.

Preferred compounds for use in the practice of the invention, are selected from the group consisting of:

1-(3,4-dimethoxyphenyl)-4-methyl-5-ethyl-7-hydroxy-8-methoxy-5H-2,3-benzodiazepine;
1-(3-hydroxy-4-methoxyphenyl)-4-methyl-5-ethyl-7,8-dimethoxy-5H-2,3-benzodiazepine;
1-(3-methoxy-4-hydroxyphenyl)-4-methyl-5-ethyl-7,8-dimethoxy-5H-2,3-benzodiazepine;
1-(3,4-dimethoxyphenyl)-4-methyl-5-ethyl-7-methoxy-8-hydroxy-5H-2,3-benzodiazepine;
or pharmaceutically-acceptable salts thereof.

More preferred compounds for use in the practice of the invention, are selected from the group consisting of:

1-(3-hydroxy-4-methoxyphenyl)-4-methyl-5-ethyl-7,8-dimethoxy-5H-2,3-benzodiazepine;
1-(3-methoxy-4-hydroxyphenyl)-4-methyl-5-ethyl-7,8-dimethoxy-5H-2,3-benzodiazepine;
or pharmaceutically-acceptable salts thereof.

According to some embodiments, there are provided the methods above wherein the compound is in the form of the substantially isolated (R)-enantiomer.

According to other embodiments, there are provided the methods above wherein the compound is in the form of the substantially isolated (S)-enantiomer.

Definitions

The term "irritable bowel syndrome" refers to a disorder, often recurrent, characterized by abnormally increased motility of the small and large intestines, producing abdominal pain, constipation, or diarrhea.

The term "nonulcer dyspepsia" refers to a disorder manifesting chronic or recurrent upper abdominal pain or discomfort for a period of more than three months' duration, with symptoms present for more than 25 percent of the time, in the absence of another organic cause.

The term "acyl" means a radical of the general formula —C(=O)—R, wherein —R is hydrogen, hydrocarbyl, amino, alkylamino, dialkylamino hydroxy or alkoxy." Examples include for example, acetyl (—C(=O)$CH_3$), propionyl (—C(=O)$CH_2CH_3$), benzoyl (—C(=O)$C_6H_5$), phenylacetyl (—C(=O)$CH_2C_6H_5$), carboethoxy (—$CO_2CH_2CH_3$), and dimethylcarbamoyl (—C(=O)N($CH_3$)$_2$). When the R group in the acetyl radical is alkoxy, alkyl amino or dialkyl amino, the alkyl portion is preferably ($C_1$–$C_6$)alkyl, more preferably ($C_1$–$C_3$)alkyl. When the R is hydrocarbyl, it is preferably ($C_1$–$C_7$)hydrocarbyl. When R is hydrocarbyl, it is preferably alkyl, more preferably ($C_1$–$C_6$) alkyl.

The term "alkyl", by itself or as part of another substituent means, unless otherwise stated, a straight, branched or cyclic chain hydrocarbon radical, including di- and multi-radicals, having the number of carbon atoms designated (i.e. $C_1$–$C_6$ means one to six carbons). Alkyl groups include straight chain, branched chain or cyclic groups, with straight being preferred. Examples include: methyl, ethyl, propyl, isopropyl, butyl, isobutyl, tert-butyl, pentyl, neopentyl, hexyl, cyclohexyl and cyclopropylmethyl. ($C_1$–$C_6$)alkyl is preferred. Most preferred is ($C_1$–$C_3$)alkyl, particularly ethyl, methyl and isopropyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred is ($C_1$–$C_6$)alkoxy. More preferred is ($C_1$–$C_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle. Examples of amino groups include: —$NH_2$, methyl amino, diethyl amino, anilino, benzyl amino, piperidinyl, piperazinyl and indolinyl. Preferred hydrocarbyl radicals are ($C_1$–$C_7$)hydrocarbyl radicals. Preferred are hydrocarbyl radicals that are alkyl radicals. More preferred is ($C_1$–$C_6$)alkyl.

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "hydrocarbyl" refers to any moiety comprising only hydrogen and carbon atoms. This definition includes for example alkyl, alkenyl, alkynyl, aryl and benzyl groups. Preferred are ($C_1$–$C_7$)hydrocarbyl.

The term "heteroalkyl" by itself or in combination with another term means, unless otherwise stated, a stable straight or branched chain radical consisting of the stated number of carbon atoms and one or two heteroatoms selected from the group consisting of O, N, and S. Nitrogen and sulfur atoms may be optionally oxidized to the N-oxide and sulfoxide or sulfone, respectively. In addition, a nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Preferred are ($C_2$–$C_6$) heteroalkyl. More preferred are ($C_2$–$C_4$)heteroalkyl. Examples include: —O—$CH_2$—$CH_2$—$CH_3$, —$CH_2$—$CH_2CH_2$—OH, —$CH_2$—$CH_2$—NH—$CH_3$, —$CH_2$—C(=O)—$CH_3$, —$CH_2$—N=N—$CH_2$—$CH_3$, —$CH_2$—S—$CH_2$—$CH_3$, —$CH_2CH_2$—S(=O)—$CH_3$ and —$CH_2$—$CH_2$—NH—$SO_2$—$CH_3$. Up to two heteroatoms may be consecutive, such as, for example, —$CH_2$—NH—$OCH_3$, or —$CH_2$—$CH_2$—S—S—$CH_3$. More preferred are heteroalkyl groups containing one or two oxygen atoms.

When two groups may "combine to form a carbocyclic or heterocyclic 5- or 6-membered ring," a carbocyclic ring is preferably saturated. Preferred heterocyclic rings are saturated rings containing one or two heteroatoms selected from N, O and S. Heterocyclic rings annulated to the benzodiazepine seven-membered ring in this way include, for example, furan, dihydrofuran, tetrahydrofuran, pyran, dihydropyran, tetrahydropyran, thiophene, dihydrothiophene, tetrahydrothiophene, pyrrole, dihydropyrrole, pyrrolidine, pyridine, dihydropyridine, tetrahydropyridine and piperidine.

When two groups may "combine to form a 5-, 6- or 7-membered heterocyclic ring," preferred heterocyclic rings are 5- or 6-membered rings containing one or two heteroatoms selected from N, O and S. More preferred are heterocyclic rings containing one heteroatom selected from N, O and S. Heterocyclic rings annulated to the benzodiazepine phenyl ring in this way include, for example, furan, dihydrofuran, dioxane, dioxolane, pyran, dihydropyran, tetrahydropyran, thiophene, dihydrothiophene, pyridine, dihydropyridine, tetrahydropyridine, piperidine, pyrrole, dihydropyrrole, imidazole, dihydroimidazole, thiazole, dihydrothiazole, oxazole, and dihydrooxazole.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The phrase "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, $4^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking sequence id A>B>C>D. The lowest ranking atom, D is oriented away from the viewer.

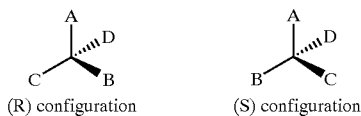

(R) configuration        (S) configuration

The term "racemate" or the phrase "racemic mixture" refers to a 50-50 mixture of two enantiomers such that the mixture does not rotate plane-polarized light.

By "(R)-enantiomer substantially free of the (S)-enantiomer" is meant a compound of formula I that comprises 80% or more by weight of the (R)-enantiomer and likewise contains 20% or less of the (S)-enantiomer as a contaminant, by weight. Likewise, By "(S)-enantiomer substantially free of the (R)-enantiomer" is meant a compound of formula I that comprises 80% or more by weight of the (S)-enantiomer and likewise contains 20% or less of the (R)-enantiomer as a contaminant, by weight.

The term "effective amount" when used to describe the amount of drug administered to a patient suffering from irritable bowel syndrome, refers to the amount of a compound that prevents or alleviates the symptoms of IBS, when administered to a patient suffering from a disorder which manifests chronic or acute symptoms of IBS.

An "effective amount" of the compound when used to describe the amount of drug administered to a patient suffering from nonulcer dyspepsia, refers to the amount of a compound that prevents or alleviates the symptoms of NUD, when administered to a patient suffering from a disorder which manifests chronic or acute symptoms of NUD.

The term "individual" or "subject" includes human beings and non-human animals. With respect to the disclosed methods of treating IBS and NUD, these terms refer, unless the context indicates otherwise, to an organism that is afflicted with or diagnosed with such a disorder.

With respect to disclosed methods of "preventing" or "delaying the onset" of IBS or NUD, these terms refer unless the context indicates otherwise, to an organism that has a medical history of IBS or NUD that manifests as a recurrent disorder.

DETAILED DESCRIPTION OF THE INVENTION

According to the present invention, compounds of formula I, and pharmaceutically acceptable salts thereof, are useful in methods of treatment or prevention of irritable bowel syndrome or nonulcer dyspepsia.

Compounds used in the methods of the present invention that comprise substantially isolated enantiomers preferably have a composition that is 85% by weight or greater of the desired enantiomer, and 15% by weight, or less, of the other enantiomer. More preferably, compounds used in methods of the present invention have a composition that is 90% by weight or greater of the desired enantiomer and 10% by weight, or less, of the other enantiomer. More preferably, compounds used in the methods of the present invention have a composition that is 95% by weight or greater of the desired enantiomer and 5% by weight, or less, of the other enantiomer. Most preferably, compounds used in the methods of the present invention have a composition that is 99% by weight or greater of the desired enantiomer and 1% by weight, or less, of the other enantiomer.

The compounds of formula I useful in the methods of the present invention may be prepared by one of several methods. These methods generally follow the synthetic strategies and procedures used in the synthesis of 2,3-benzodiazepines such as tofisopam and tofisopam analogs. See U.S. Pat. Nos. 3,736,315 and 4,423,044 (tofisopam syntheses) and Horvath et al., *Progress in Neurobiology* 60(2000) p.309–342 and references cited therein (preparation of tofisopam and analogs thereof), the disclosures of which are incorporated herein by reference. In the synthesis methods that follow, the products of the chemical synthesis are racemic compounds of formula I. The racemic mixture may be subsequently separated using known methods of resolution to produce the (R)-enantiomer substantially free of the corresponding (S)-enantiomer, and the (S)-enantiomer substantially free of the corresponding (R)-enantiomer.

2,3-Benzodiazepines of formula I may be synthesized from the corresponding 2-benzopyrilium salt H by reaction with hydrazine hydrate, wherein X⁻ is a counterion such as, for example perchlorate:

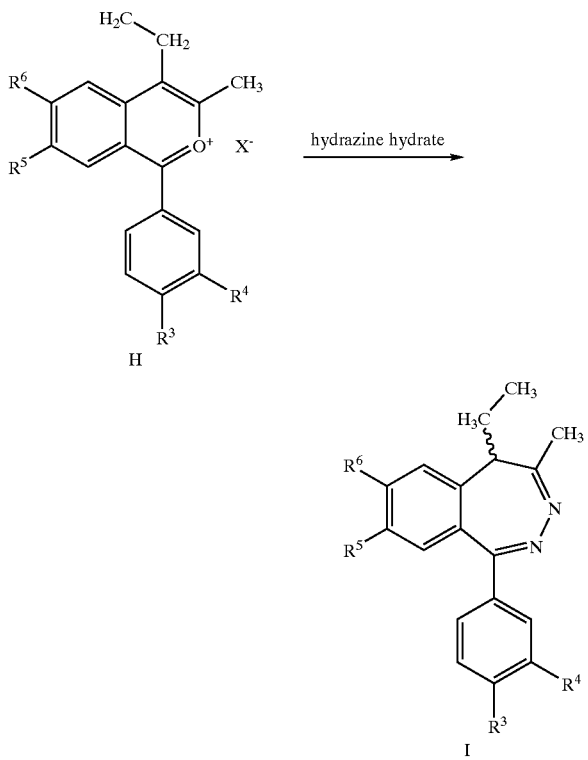

Accordingly, hydrazine hydrate (98%, approximately 3 equivalents based on the 2-benzopyrylium salt) is added dropwise to a stirred solution of the 2-benzopyrylium salt H in glacial acetic acid (approximately 1 mL/3 mmol of 2-benzopyrylium salt). During this operation, the solution is maintained at an elevated temperature, preferably, 80–100° C. The solution is then maintained a higher elevated temperature, preferably 95–100° C., for about one hour. Then the reaction mixture is diluted with 2% aqueous sodium hydroxide solution (approximately 3 equivalents based on the 2-benzopyrylium salt) and cooled. The product 2,3-benzodiazepine separates as a solid and is removed by filtration, washed with water and dried. The crude product may be purified by taking it up in a polar aprotic solvent such as dimethylformamide (DMF) at an elevated temperature, preferably 100–130° C., and decolorizing the solution with activated carbon. The carbon is removed by filtration and the filtered solution is diluted with water. The purified product precipitates out of the solution and is collected by filtration.

See Kórósi et al., U.S. Pat. No. 4,322,346, the entire disclosure of which is incorporated herein by reference, disclosing three variations of the reaction protocol for preparing a substituted 2,3-benzodiazepine from the precursor benzopyrilium salt.

Retrosynthetically, the intermediate benzopyrilium salt, H, may be prepared from one of several starting materials. According to one such method, illustrated in Scheme 1, intermediate H is prepared from the corresponding aryl ethanol derivative D via the isochroman intermediate F; wherein X⁻ is a counterion such as, for example, perchlorate:

Scheme 1

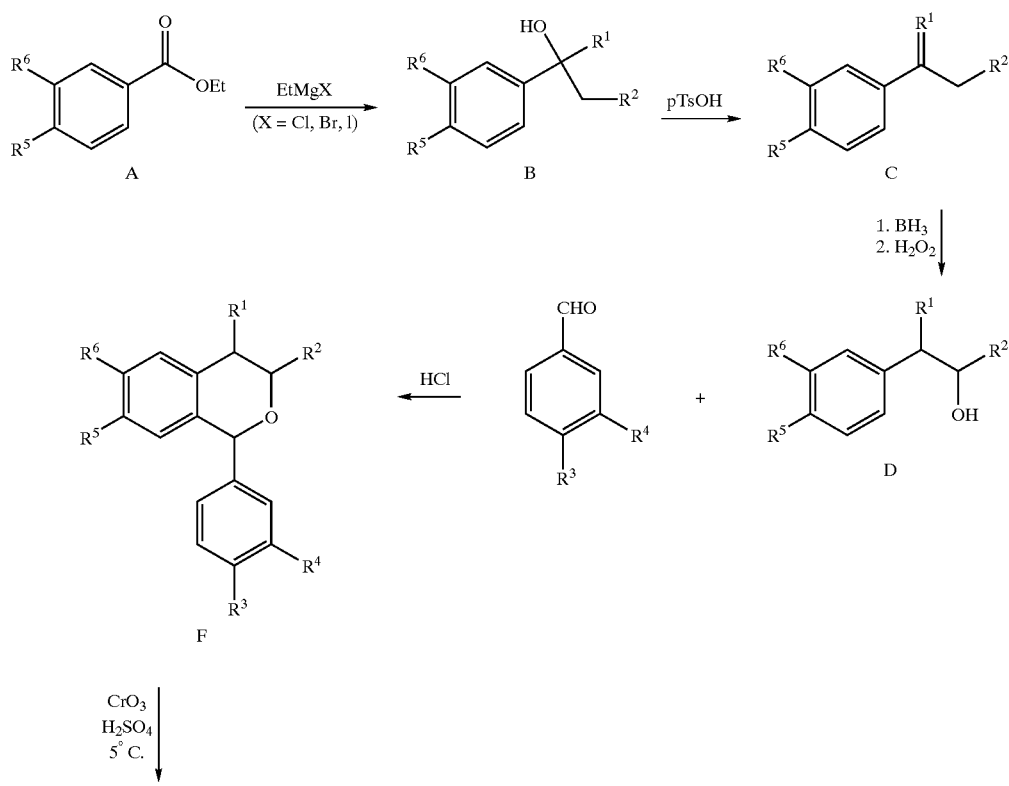

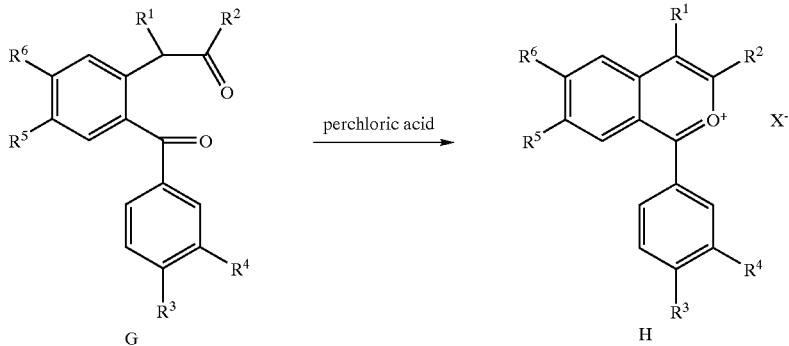

According to Scheme 1, 3,4-disubstituted ethylbenzoate, A is dissolved in a suitable solvent, preferably ether and cooled to 0° C. Two equivalents of a selected Grignard reagent are added dropwise and the reaction is allowed to warm to room temperature and monitored for disappearance of starting material. When the reaction is complete, it may be quenched with a proton source such as acetic acid. Volatiles are removed in vacuo, and the product B is used for the next step without purification.

The α-substituted benzyl alcohol, B, is taken up in a high boiling solvent such as toluene and a catalytic amount of para-toluene sulfonic acid (p-TsOH). The mixture is warmed to reflux and may be monitored for disappearance of starting materials. When the reaction is complete, the volatiles are removed in vacuo and the crude product C is purified by column chromatography.

The substituted styrene, C is hydroxylated under anti-Markovnikov conditions to give intermediate phenylethyl alcohol D. A solution of D, and of a substituted benzaldehyde, E (1.2 eq) are dissolved in anhydrous dioxane. The resulting solution is then saturated with gaseous HCl and warmed, preferably to reflux temperature for about one hour. The mixture is then cooled to room temperature, poured into water, basified, preferably with aqueous sodium hydroxide and extracted with an organic solvent, preferably ethyl acetate. The extract is dried, filtered and concentrated under vacuum. The resulting residue is purified, preferably by crystallization to yield F.

To a stirred, cooled, (preferably to 0–5° C.) solution of F (2 g) in acetone (30 mL), is added dropwise a solution of chromium trioxide (2 g) in 35% sulfuric acid (20 mL); added at a rate such that the reaction temperature remains below 5° C. After the addition is complete, the reaction mixture is allowed to rise to room temperature and is stirred at room temperature for two hours. The reaction mixture is then poured into water and extracted with an organic solvent, preferably ethyl acetate. The organic extract is washed with water and then with ice-cold 10% aqueous sodium hydroxide. The aqueous alkaline fraction is then acidified, preferably with dilute aqueous hydrochloric acid and extracted with an organic solvent, preferably, chloroform. The chloroform extract is dried, filtered and concentrated under vacuum to give G. The crude residue may further be purified by column chromatography.

The 2-α-acyl hydrocarbylbenzophenone, G (5 g) is dissolved in glacial acetic acid (15 mL). To this mixture is added 60% perchloric acid (7.5 mL). The resulting mixture is warmed to 100° C. (steam bath) for three minutes. The mixture is allowed to cool to room temperature. Crystallization of the crude product may begin spontaneously at this point or may be induced by addition to the reaction mixture of ether or ethyl acetate. The product 2-benzopyrylium salt H is removed by filtration and purified by recrystallization, preferably from ethanol or glacial acetic acid/ethyl acetate.

A synthetic sequence, similar to that outlined above, for preparation of 2,3-benzodiazepines is disclosed in U.S. Pat. No. 3,736,31 5, the entire disclosure of which is incorporated herein by reference. Synthetic strategies for preparation of 2,3-benzodiazepines are also disclosed in Horvath et al., *Progress in Neurobiology* 60(2000) p309–342 and references cited therein; the entire disclosures of which are incorporated herein by reference.

Alternative methods for preparation of intermediate H start with an aryl acetonide or indanone starting material. See Kunnetsov, E. V., and Dorofeenko, G. N., *Zh. Org. Khim.*, 6, 578–581; and M. Vajda, *Acia Chem. Acad. Sci. Hung.*, 40, p.295–307, 1964, respectively. Another variation for preparing 2,3-benzodiazepines is illustrated in Scheme 2 and 3 (Examples 1 and 2). The synthesis proceeds from intermediate G without isolation of the intermediate benzopyrilium salt H.

Resolution of 5-substituted-2,3-benzodiazepines of formula I

The synthetic procedures shown (or referenced) above result in racemic 2,3-benzodiazepines of formula I. The racemate must be resolved in order to isolate the individual (R)- and (S)-enantiomers. Enantiomeric resolution may be achieved by converting racemic compositions of formula I to a pair of diastereomers by either covalently bonding to an optically active moiety, or by salt formation with an optically active base or acid. Either of these two methods provides a molecule with a second chiral center, thus generating a pair of diastereomers. This diastereomeric pair is then separated by conventional methods such as for example, crystallization or chromatography.

Racemic compounds of formula I may be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic tofisopam. See Hungarian Patent 178516 and also Toth et al., *J. Heterocyclic Chem.*, 20:09–713 (1983), the entire disclosures of which are incorporated herein by reference.

Alternatively, racemic compounds of formula I may be derivatized via, for example, acylation of the aromatic hydroxy moiety with a chiral acylating reagent such as, for example, (S)-mandelic acid. The resulting ester, has a second chiral center, and thus exists as a diastereomeric pair separable using conventional methods such as crystallization or chromatography. Following the separation, the chiral moiety with which the compound was derivatized, may be removed.

Racemic compounds of formula I may be separated without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic 2,3-benzodiazepines include:

(i) macrocyclic glycopeptides, such as silica-bonded vancomycin which contains 18 chiral centers surrounding three pockets or cavities;

(ii) chiral $\alpha_1$-acid glycoprotein;

(iii) human serum albumin; and (iv) cellobiohydrolase (CBH).

Chiral $\alpha_1$-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme that has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos el al. (*J. Chromatogr.*, 709 265 (1995)), the entire disclosures of which are incorporated herein by reference, discloses another method for resolving racemic tofisopam by chiral chromatography using a chiral $\alpha_1$-acid glycoprotein as a stationary phase on a CHIRAL-AGP™ column (ChromTech, Cheshire, UK). This method separates the (R)- and (S)-enantiomers and also resolves the two conformers (discussed below) of each enantiomer. These methods, may be used to separate racemic 2,3-benzodiazepines of formula I into individual (R)- and (S)-enantiomers. The Chirobiotic V™ column is available in a semi-preparative size as employed for the above separation 500 mm×10 mm). In addition, the stationary phase of the Chirobiotic V™ column is commercially available in bulk for packing of preparative chromatography columns with larger sample capacity.

In addition to existing as (R)- and (S)-enantiomers, 2,3-benzodiazepines of formula I, also exist in two stable conformations that may be assumed by the benzodiazepine ring as generally depicted below.

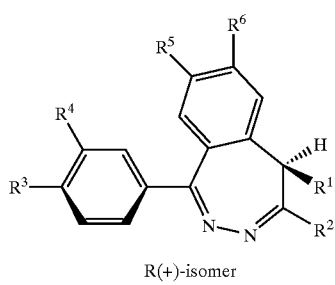

R(+)-isomer

-continued

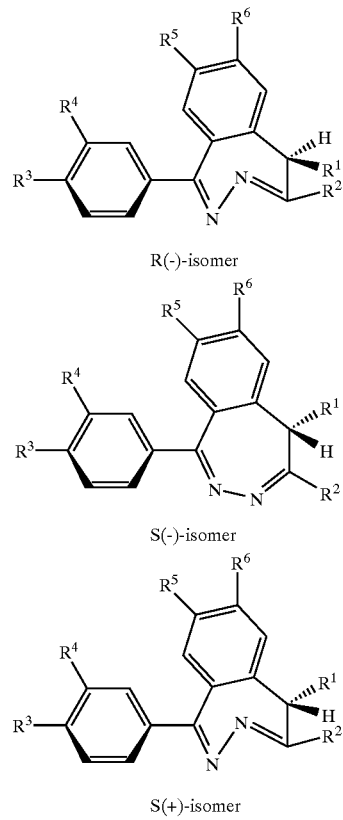

R(-)-isomer

S(-)-isomer

S(+)-isomer

The present invention includes compositions and methods as described herein that use any and all observable conformations of compounds of formula I.

The compound used in the compositions and methods of the present invention may take the form of a pharmaceutically-acceptable salt. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process or in the process of resolving enantiomers from a racemic mixture. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable pharmaceutically acceptable base addition salts of compounds of formula I, include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds useful in the methods of the invention may be administered to individuals (mammals, including animals and humans) afflicted with IBS or NUD.

For treating or preventing irritable bowel syndrome or nonulcer dyspepsia, the specific dose of a compound of formula I, or a substantially isolated enantiomer thereof to obtain therapeutic benefit will, of course, be determined by the particular circumstances of the individual patient including, the size, weight, age and sex of the patient. Also determinative will be the nature and stage of the disease and the route of administration. For example, a daily dosage of from about 100 to 1500 mg/kg/day may be utilized. Preferably, a daily dosage of from about 100 to 1000 mg/kg/day may be utilized. More preferably, a daily dosage of from about 100 to 500 mg/kg/day may be utilized. Higher or lower doses are also contemplated.

For prophylactic administration, the compound should be administered far enough in advance of a recurrence of symptoms such that the compound is able to reach the site of action in sufficient concentration to exert a therapeutic effect. The pharmacokinetics of specific compounds may be determined by means known in the art and tissue levels of a compound in a particular individual may be determined by conventional analyses.

The compound may be administered in the form of a pharmaceutical composition comprising at least one compound of formula I in combination with a pharmaceutically acceptable carrier. The active ingredient in such formulations may comprise from 0.1 to 99.99 weight percent. By "pharmaceutically acceptable carrier" is meant any carrier, diluent or excipient that is compatible with the other ingredients of the formulation and not deleterious to the recipient.

The compound may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For administration in the therapy of chronic disorders, the compound may optionally be localized in a depot for controlled or sustained release to the circulation, or controlled or sustained release to a local site such as for example the gastrointestinal tract or a portion thereof.

The pharmaceutically acceptable carrier is selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions useful in the methods of the present invention may also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms may provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

Biodegradable microparticles may be used in the controlled-release formulations of this invention. For example, U.S. Pat. No. 5,354,566 discloses a controlled-release powder that contains the active ingredient. U.S. Pat. No. 5,733,566 describes the use of polymeric microparticles that release antiparasitic compositions. These patents are incorporated herein by reference.

The controlled-release of the active ingredient may be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the compound of formula I in the pharmaceutical composition. In another embodiment, the controlled-release component may be biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The practice of the invention is illustrated by the following non-limiting examples.

EXAMPLES

Example 1

Synthesis of racemic-1-(3-hydroxy-4-methoxyphenyl)-4-methyl-5-ethyl-7,8-dimethoxy-5H-2,3-benzodiazepine Racemic-1-(3-hydroxy-4-methoxyphenyl)-4-methyl-5-ethyl-7,8-dimethoxy-5H-2,3-benzodiazepine was synthesized according to the route of Scheme 2.

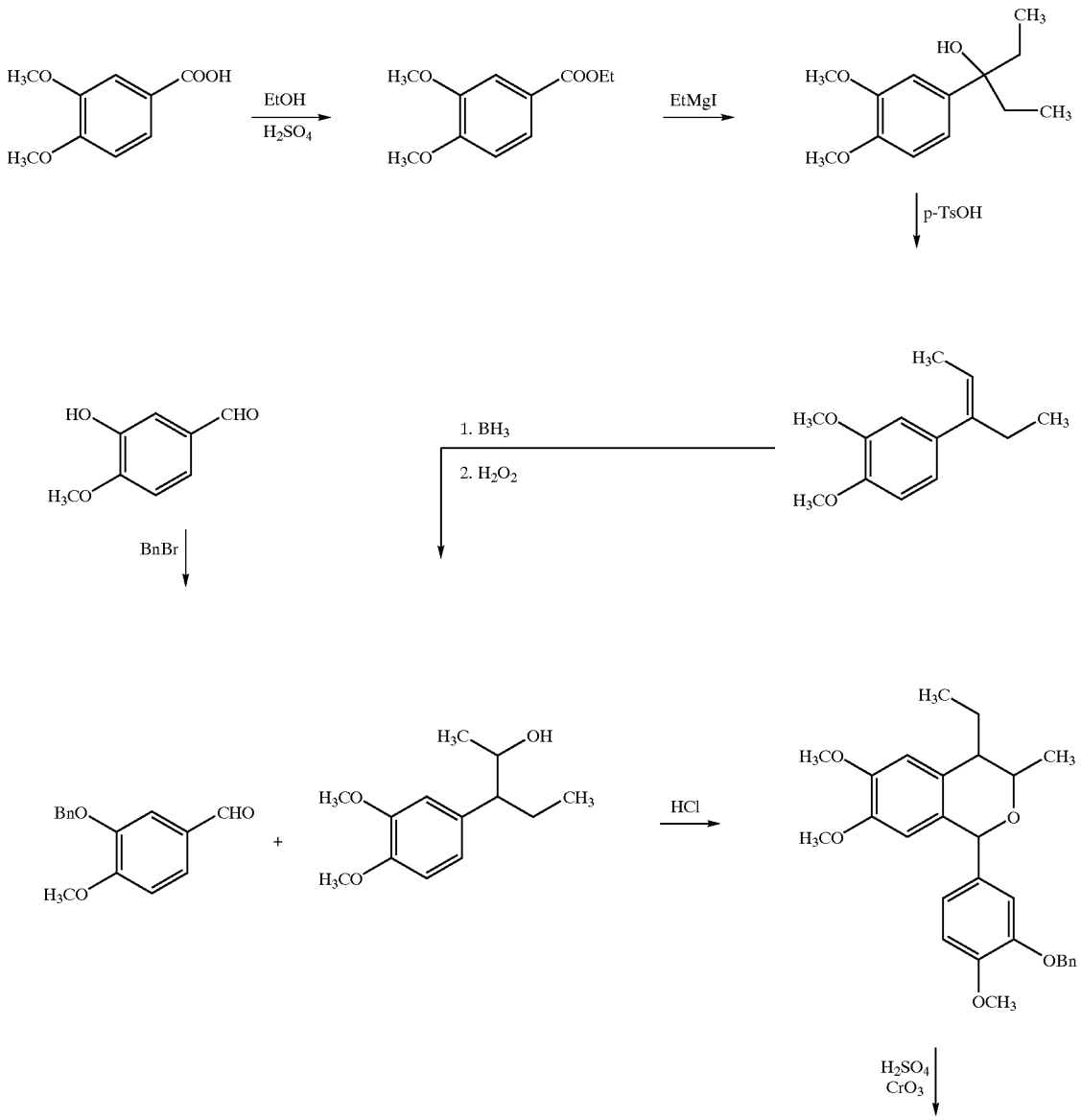

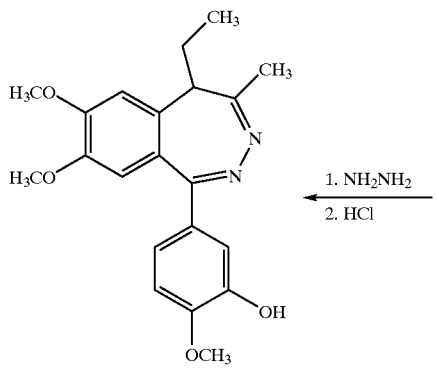

-continued

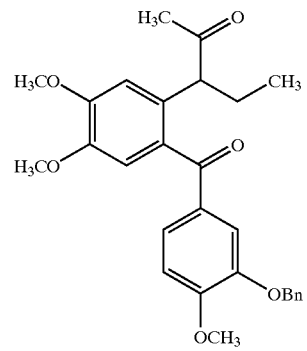

A. Esterification of 3,4-dimethoxybenzoic acid to yield ethyl-3,4- dimethoxybenzoate ([3943-77-9]).

A solution of 200 g of 3,4-dimethoxybenzoic acid and 35 g of concentrated sulfuric acid in 600 mL of absolute ethanol was heated at reflux overnight. The mixture was concentrated and the residue poured into water. Methylene chloride was added and the solution washed successively with water, dilute sodium bicarbonate and water, then dried and concentrated. The residue was recrystallized from acetone/hexane.

B. Addition of ethyl magnesium iodide to ethyl-3,4-dimethoxybenzoate acid to yield 3-(3,4-dimethoxyphenyl)pentan-3-ol.

A solution of 4.8 mL of iodoethane in 20 mL of ether was added dropwise to a suspension of 1.5 g of magnesium turnings in 10 mL of ether. After 5 mL of the iodoethane solution had been added, a few grains of iodine were added and the mixture was heated to induce formation of the Grignard reagent. The remaining iodoethane solution was then added. After the Grignard formation was complete, a solution of 5 g of ethyl 3,4-dimethoxybenzoate in ether was added and the mixture was allowed to stir at room temperature overnight. The reaction was quenched by addition of saturated ammonium chloride. The mixture was extracted with ether. The combined ether extracts were dried and concentrated to an oily residue. Yield: 5 g.

C. Elimination of $H_2O$ from 3-(3,4-dimethoxyphenyl)pentan-3-ol to yield 4-((1Z)-1-ethylprop-1-enyl)-1,2-dimethoxybenzene.

A solution of 5 g of crude 3-(3,4-dimethoxyphenyl)pentan-3-ol and 0.25 g of p-tolenesulfonic acid in 80 mL of benzene was heated at reflux for 1 hr with azeotropic removal of water. The mixture was then filtered through a pad of sodium bicarbonate and the filtrate concentrated. The residue was purified by distillation under reduced pressure. Yield: 2.9 g.

D. Addition of $H_2O$ to 4-((1Z)-1-ethylprop-1-enyl)-1,2-dimethoxybenzene to yield 3-(3,4-dimethoxyphenyl)pentan-2-ol.

To a solution of 26 g of 4-((1Z)-1-ethylprop-1-enyl)-1,2-dimethoxybenzene in tetrahydrofuran at 0° C. was added 189 mL of a 1.0M solution of borane-tetrahydrofuran complex in tetrahydrofuran. The mixture was stirred for 3 hr at 0° C., then 35.6 mL of 50% hydrogen peroxide was added, with simultaneous addition of 5M sodium hydroxide to maintain the mixture at pH 8. The mixture was extracted with ether. The combined ether extracts were dried and concentrated.

E. Benzylation of 3-hydroxy-4-methoxybenzaldehyde to yield 4-methoxy-3-(phenylmethoxy)benzaldehyde ([6346-05-0]).

A solution of 100 g of 3-hydroxy-4-methoxybenzaldehyde and 135 g of benzyl bromide in 500 mL of acetone containing a suspension of 137 g of potassium carbonate was heated at reflux overnight. The mixture was filtered, the filtrate concentrated and the residue recrystallized from toluene/hexane. Yield: 65 g.

F. Reaction of 3-(3,4-dimethoxyphenyl)pentan-2-ol with 4-methoxy-3-(phenyl-methoxy)benzaldehyde to yield 4-(4-ethyl-6,7-dimethoxy-3-methyliso-chromanyl)-1-methoxy-2-(phenylmethoxy)benzene.

A solution of 14 g of 4-methoxy-3-(phenylmethoxy)benzaldehyde and 15 g of 3-(3,4-dimethoxyphenyl)pentan-2-ol in 0.3 L of dioxane was saturated with hydrogen chloride gas. The mixture was heated at reflux for 3 hr, saturated again with hydrogen chloride gas and allowed to stir at room temperature overnight. It was then poured into water, basified with dilute sodium hydroxide and extracted with methylene chloride. The combined methylene chloride extracts were dried and concentrated.

G. Ring-opening of 4-(4-ethyl-6,7-dimethoxy-3-methyliso-chromanyl)-1-methoxy-2-(phenylmethoxy)benzene to yield 3-(4,5-dimethoxy-2-{[4-methoxy-3-(phenylmethoxy)phenyl]carbonyl}phenyl)pentan-2-one.

To a solution of 30 g of crude 4-(4-ethyl-6,7-dimethoxy-3-methyliso-chromanyl)-1-methoxy-2-(phenylmethoxy) benzene in 450 mL of acetone at 5° C. was added a solution of 30 g of chromic oxide in 300 mL of 35% sulfuric acid. The mixture was stirred at room temperature for 2 hr, neutralized by adding cold 10% sodium hydroxide and concentrated to remove acetone. Then, water was added and the mixture was extracted with methylene chloride. The combined methylene chloride extracts were dried and concentrated. The residue was purified by column chromatography on silica gel. Yield: 10 g H. Debenzylation of 3-(4,5-dimethoxy-2-{[4-methoxy-3-(phenylmethoxy)-phenyl]carbonyl}phenyl)pentan-2-one to yield 3-{2-[(3-hydroxy-4-methoxy-phenyl)carbonyl]-4,5-dimethoxyphenyl}pentan-2-one.

A solution of 10 g of 3-(4,5-dimethoxy-2-{[4-methoxy-3-(phenylmethoxy)-phenyl]carbonyl}phenyl)pentan-2-one in methylene chloride containing a suspension of 0.9 g of 10% palladium on carbon was hydrogenated at 80 psi for 1 hr. The mixture was filtered through diatomaceous earth and the filtrate concentrated. Yield: 6.5 g I. Annulation of 3-{2-[(3-hydroxy-4-methoxyphenyl)carbonyl]-4,5-dimethoxyphenyl}pentan-2-one by reaction with hydrazine to yield 1-(3-hydroxy-4-methoxyphenyl)-4-methyl-5-ethyl-7,8-dimethoxy-5H-2,3-benzodiazepine.

A solution of 6.5 g of 3-{2-[(3-hydroxy-4-methoxyphenyl)carbonyl]-4,5-dimethoxyphenyl}pentan-2-one and 2.2 mL of hydrazine in 130 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 0.97 g The product 1-(3-hydroxy-4-methoxyphenyl)-4-methyl-5-ethyl-7,8-dimethoxy-5H-2,3-benzodiazepine was analyzed by HPLC, elemental analysis, GC/MS, proton NMR and differential scanning calorimetry (DSC). The data are as follows:

Purity: 99.29% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

DSC: Temperature program 100° C. to 300° C. at 5° C./min, indicated molar purity =99.75% and melting point of 158.6° C.

Elemental analysis (calculated/analysis): %C, 68.09/68.08; %H, 6.61/6.57; N, 7.53/7.35. Calculated values include 0.02 equivalents of ethyl acetate and 0.09 equivalents of residual water.

NMR (DCCl$_3$) (performed on GE QE 300): 1.08 ppm (t, 3H); 1.99 (s, 3H); 2.11 (m, 2H); 2.75 (m, 1H); 3.75 (s, 3H); 3.93 (s, 3H); 3.97 (s, 3H); 6.46 (bs, 1H); 6.72 (s, 1H); 6.86 (m, 2H); 7.18 (d, 1H); 7.48 (s, 1H).

Example 2

Synthesis of 1-(3,4-dimethoxyphenyl)-4-methyl-5-ethyl-7-methoxy-8-hydroxy-5H-2,3-benzodiazepine Racemic 1-(3,4-dimethoxyphenyl)-4-methyl-5-ethyl-7-methoxy-8-hydroxy-5H-2,3-benzodiazepine was synthesized according to the route of Scheme 3.

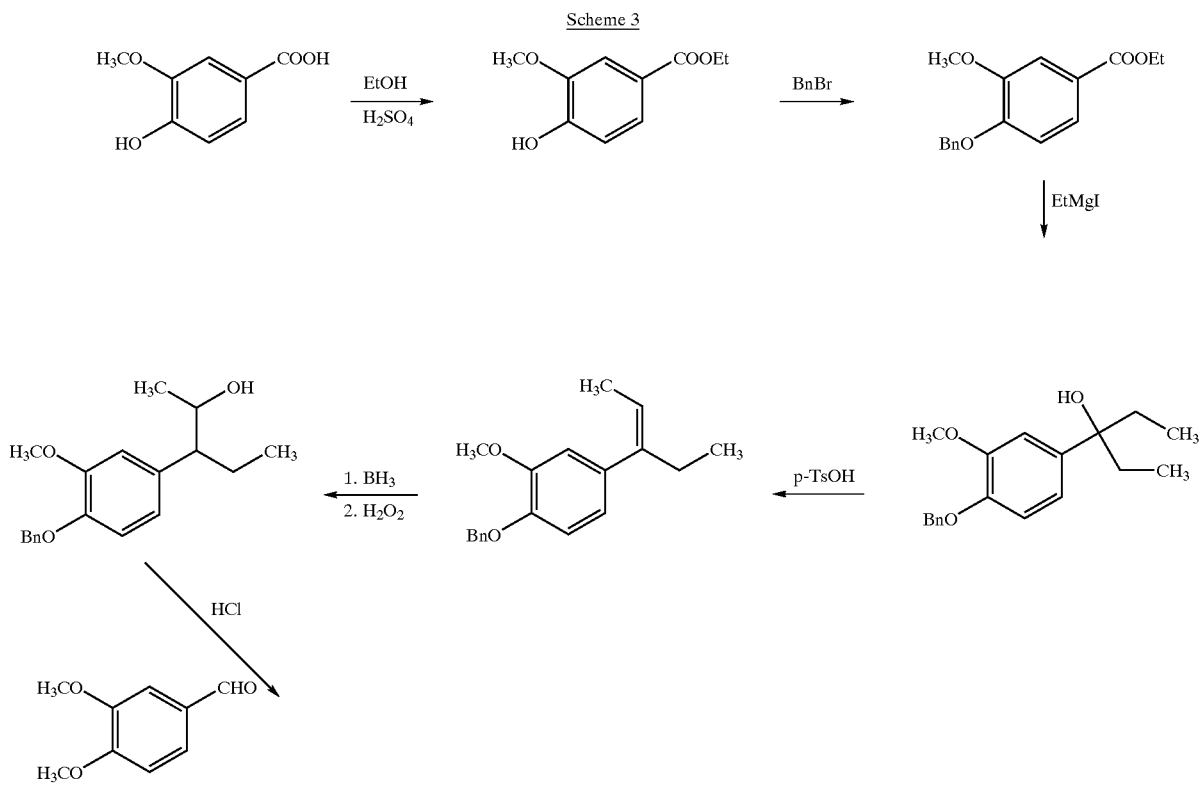

Scheme 3

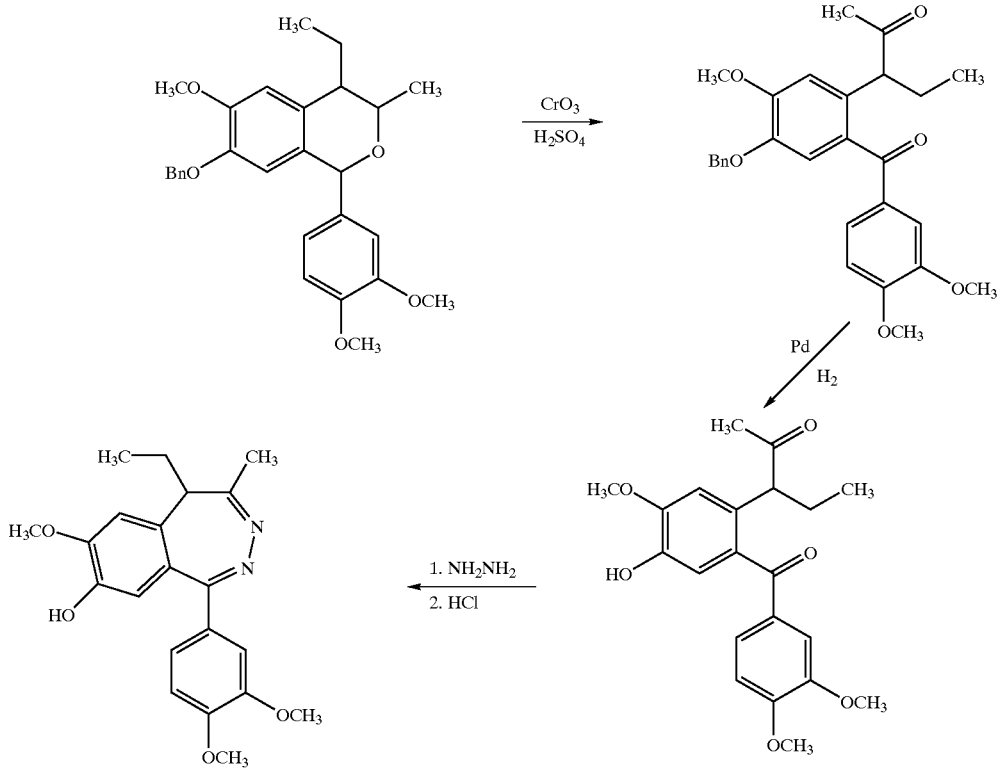

A. Esterification of 3-methoxy-4-hydroxybenzoic acid to yield ethyl-3-methoxy-4-hydroxybenzoate.

A solution of 100 g of 3-methoxy-4-hydroxybenzoic acid and 17 g of concentrated sulfuric acid in 300 mL of absolute ethanol was heated at reflux overnight. The mixture was concentrated and the residue poured into water. Methylene chloride was added and the solution washed successively with water, dilute sodium bicarbonate and water, then dried and concentrated. Yield: 118 g B. Benzylation of ethyl-3-methoxy-4-hydroxybenzoate to yield ethyl-3-methoxy-4-benzyloxybenzoate.

A solution of 118 g of ethyl-3-methoxy-4-hydroxybenzoate and 86 mL of benzyl bromide in 600 mL of acetone containing a suspension of 124 g of potassium carbonate was heated at reflux overnight. The mixture was filtered, the filtrate concentrated and the residue recrystallized from acetone.

C. Addition of ethyl magnesium iodide to ethyl-3-methoxy-4-benzyloxybenzoate to yield 3-(3-methoxy-4-benzyloxyphenyl)pentan-3-ol.

Iodoethane (112 mL) was added dropwise to a suspension of 35 g of magnesium turnings in 160 mL of ether. After the formation of ethyl magnesium iodide was complete, a solution of 142 g of ethyl 3-methoxy-4-benzyloxybenzoate in ether was added and the mixture was allowed to stir at room temperature for 3 days. The reaction was quenched by addition of saturated ammonium chloride. The layers were separated and the ether layer was dried and concentrated to an oily residue. Yield: 110 g.

D. Elimination of $H_2O$ from 3-(3-methoxy-4-benzyloxyphenyl)pentan-3-ol to yield 4-((1Z)-1-ethylprop-1-enyl)-1-benzyloxy-2-methoxybenzene.

A solution of 110 g of crude 3-(3-methoxy-4-benzyloxyphenyl)pentan-3-ol and 7 g of p-tolenesulfonic acid in 2 L of benzene was heated at reflux for 4 hr with azeotropic removal of water. The mixture was then filtered through a pad of sodium bicarbonate and the filtrate concentrated. The residue was purified by column chromatography on neutral alumina.

E. Addition of $H_2O$ to 4-((1Z)-1-ethylprop-1-enyl)-1-benzyloxy-2-methoxybenzene to yield 3-(3-methoxy-4-benzyloxyphenyl)pentan-2-ol.

To a solution of 96 g of 4-((1Z)-1-ethylprop-1-enyl)-1-benzyloxy-2-methoxybenzene in tetrahydrofuran at 0° C. was added 510 mL of a 1.0M solution of borane-tetrahydrofuran complex in tetrahydrofuran. The mixture was stirred for 3 hr at 0° C., then 204 mL of 25% hydrogen peroxide was added. The mixture was adjusted to pH 8 by addition of 5M sodium hydroxide and extracted with ether. The combined ether extracts were dried and concentrated. Yield: 102 g.

F. Reaction of 3-(3-methoxy-4-benzyloxyphenyl)pentan-2-ol with 3,4-dimethoxybenzaldehyde to yield 4-(4-ethyl-6-methoxy-7-benzyloxy-3-methyliso-chromanyl)-1,2-dimethoxybenzene.

A solution of 46 g of 3,4-dimethoxybenzaldehyde and 100 g of crude 3-(3-methoxy-4-benzyloxyphenyl)pentan-2-ol in 0.3 L of dioxane was saturated with hydrogen chloride gas.

The mixture was heated at reflux for 3 hr, then poured into water, basified with dilute sodium hydroxide and extracted with methylene chloride. The combined methylene chloride extracts were dried and concentrated.

G. Ring-opening of 4-(4-ethyl-6-methoxy-7-benzyloxy-3-methyliso-chromanyl)-1,2-dimethoxybenzene to yield 3-(4-benzyloxy-5-methoxy-2- {[3,4-dimethoxyphenyl]carbonyl}phenyl)pentan-2-one.

To a solution of 50 g of crude 4-(4-ethyl-6-methoxy-7-benzyloxy-3-methyliso-chromanyl)-1,2-dimethoxybenzene in acetone at 5° C. was added a solution of 50 g of chromic oxide in 500 mL of 35% sulfuric acid. The mixture was stirred at room temperature for 2 hr, neutralized by adding cold 10% sodium hydroxide and concentrated to remove acetone. Water was added and the mixture extracted with methylene chloride. The combined methylene chloride extracts were dried and concentrated. The residue was purified by column chromatography on silica gel. Yield: 18 g H. Debenzylation of 3-(4-benzyloxy-5-methoxy-2-{[3,4-dimethoxy-phenyl]carbonyl}phenyl)pentan-2-one to yield 3-{2-[(3,4-dimethoxy-phenyl)carbonyl]-4-hydroxy-5-methoxyphenyl}pentan-2-one.

A solution of 18 g of 3-(4-benzyloxy-5-methoxy-2-{[3,4-dimethoxy-phenyl]carbonyl}phenyl)pentan-2-one in methylene chloride containing a suspension of 2 g of 10% palladium on carbon was hydrogenated at 80 psi for 1 hr. The mixture was filtered through diatomaceous earth and the filtrate concentrated. Yield: 15 g I. Annulation of 3-{2-[(3,4-dimethoxy-phenyl)carbonyl]-4-hydroxy-5-methoxyphenyl}pentan-2-one by reaction with hydrazine to yield 1-(3,4-dimethoxyphenyl)-4-methyl-5-ethyl-7-methoxy-8-hydroxy-5H-2,3-benzodiazepine.

A solution of 14 g of 3-{2-[(3,4-dimethoxy-phenyl)carbonyl]-4-hydroxy-5-methoxyphenyl}pentan-2-one and 4.7 mL of hydrazine in 280 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 1.5 g The product 1-(3,4-dimethoxyphenyl)-4-methyl-5-ethyl-7-methoxy-8-hydroxy-5H-2,3-benzodiazepine was analyzed by HPLC, elemental analysis, GC/MS, proton NMR and differential scanning calorimetry (DSC). The data are as follows:

Purity: 98.36% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

Differential scanning calorimetry (DSC): Temperature program 100° C. to 300° C. at 5° C./min, indicated molar purity=99.14% and melting point of 146.2° C.

Elemental analysis (calculated/analysis): %C, 68.14/68.12; %H, 6.63/6.63; N, 7.43/7.20. The calculated values include 0.1M of residual ethyl acetate.

NMR (DCCl$_3$) (performed on GE QE 300): 1.08 ppm (t, 3H); 1.96 (s, 3H); 2.10 (m, 2H); 2.77 (m, 1H); 3.91 (s, 3H); 3.93 (s, 3H); 3.98 (s, 3H); 5.73 (bs, 1H); 6.70 (s, 1H); 6.80 (d, 1H); 6.95 (s, 1H); 7.00 (d, 1H); 7.58 (s, 1H).

Example 3

Resolution of 1-(3-hydroxy-4-methoxyphenyl)-4-methyl-5-ethyl-7,8-dimethoxy-5H-2,3-benzodiazepine The enantiomers of racemic-1-(3-hydroxy-4-methoxyphenyl)-4-methyl-5-ethyl-7,8-dimethoxy-5H-2,3-benzodiazepine are resolved by chiral chromatography as follows.

Racemic-1-(3-hydroxy-4-methoxyphenyl)-4-methyl-5-ethyl-7,8-dimethoxy-5H-2,3-benzodiazepine is loaded onto a semipreparative (500 mm×10 mm) Chirobiotic V column (ASTEC, Whippany, N.J.). Elution of the enantiomeric mixture with methyl-tert-butyl ether/acetonitrile (90/10 V/V), at a flow rate of 40 mL/min, is monitored at 310 nm. Fraction size is 10–20 mL and fractions are subjected to analytical chromatography using the same solvent composition on an analytical (150×4.6 mm) Chirobiotic V column. The fractions containing each isolated enantiomer are processed by removing the elution solvent in vacuo.

Example 4

Colonic Propulsion Study in the Mouse

This model is predictive of agents that may be used to treat the alterations in propulsion of intestinal contents that occur in individuals diagnosed with IBS. The model is very sensitive to test compounds producing inhibitory effects on propulsive motor activity, but is not sensitive to test articles increasing colonic propulsive motility. The model provides a direct measure of colonic propulsion. Thus, a test compound that slows the rate at which a glass bead is expelled, is predicted to have utility in the treatment of IBS, This test is also used to evaluate test articles with potential to produce constipation, antidiarrheal activity, or have selective visceral anti-nociceptive activity in addition to being used as an animal model for irritable bowel syndrome.

For the present example, seventy test animals (female, 6 week old Swiss Webster mice, 18–30 g) were divided into 7 groups of 10 animals each for administration of six test compounds and vehicle alone as a control.

Each animal was dosed (IP) with either a compound of formula I, one of two related 2,3-benzodiazepines or vehicle alone. Thirty minutes after dosing, a 3 mm glass bead was inserted through the anus to a depth of 2 cm into the distal colon using a glass rod. The test animals were observed for expulsion of the bead and the time was noted. Any test animal that had not expelled the bead within a cut-off time of 30 minutes was sacrificed and the position of the bead in the lumen of the colon was verified.

The test animals were observed for signs of gross toxicity and/or behavioral changes during the 60–90 minute interval after dosing. Such observations included gross evaluation of skin and fur, eyes and mucous membranes, respiratory, circulatory, autonomic and central nervous system, somatomotor activity and behavioral patterns. Particular attention was directed to observation of tremors, convulsions, salivation, diarrhea, sleep and coma. No signs of gross toxicity were observed. Mean and standard error of the mean were calculated for the expulsion times for each group. The data are summarized in Table 1 below.

TABLE 1

The Glass Bead Test of Colonic Propulsive Motility in Mice.

| Test Compound | Dose mg/kg IP | Expulsion Time Mean ± SEM | % Inhibition |
|---|---|---|---|
| Vehicle | 0 | 13.3 ± 3.7 | — |
| 1-(3-hydroxy-4-methoxyphenyl)-4-methyl-5-ethyl-7,8-dimethoxy-5H-2,3-benzodiazepine** | 32 | 20.3 ± 3.5 | 42 |
| 1-(3,4-dimethoxyphenyl)-4-methyl-5-ethyl-7-methoxy-8-hydroxy-5H-2,3-benzodiazepine** | 32 | 17.2 ± 3.5 | 23 |
| 1-(3-methoxy-4-hydroxyphenyl)-4-methyl-5-ethyl-7,8-dimethoxy-5H-2,3-benzodiazepine** | 32 | 20.0 ± 3.1 | 40* |
| 1-(3,4-dimethoxyphenyl)-4-methyl-5-ethyl-7-hydroxy-8-methoxy-5H-2,3-benzodiazepine** | 32 | 6.9 ± 3.7 | 22 |
| 1-(3-methoxy-4-hydroxyphenyl)-4-methyl-5-ethyl-7-hydroxy-8-methoxy-5H-2,3-benzodiazepine‡ | 32 | 12.0 ± 3.2 | 0 |
| 1-(3-hydroxy-4-methoxyphenyl)-4-methyl-5-ethyl-7-hydroxy-8-methoxy-5H-2,3-benzodiazepine‡ | 32 | 10.7 ± 3.4 | 0 |

*Statistically significant inhibition of time for bead expulsion, p, 0.001 Kruskal-Wallis test
**Compounds of formula I
‡Test compounds for comparison.

The data show that compounds of the invention, particularly 1-(3-methoxy-4-hydroxyphenyl)-4-methyl-5-ethyl-7,8-dimethoxy-5H-2,3-benzodiazepine and 1-(3-hydroxy-4-methoxyphenyl)-4-methyl-5-ethyl-7,8-dimethoxy-5H-2,3-benzodiazepine demonstrate substantial inhibition of colonic propulsion. Thus compounds of formula 1 are predicted by this model to be useful in the treatment of the altered colonic propulsion associated with IBS.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating or preventing irritable bowel syndrome or nonulcer dyspepsia in an individual in need of such treatment, comprising administering to the individual an effective amount of at least one compound according to formula I:

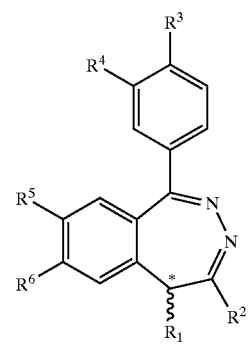

wherein:

$R^1$ is —($C_1$–$C_7$)hydrocarbyl or —($C_2$–$C_6$)heteroalkyl;

$R^2$ is —H or —($C_1$–$C_7$)hydrocarbyl;

wherein $R^1$ and $R^2$ may combine to form a carbocyclic 5-or 6-membered ring;

one of phenyl substituents $R^3$, $R^4$, $R^5$ or $R^6$ is —OH and the remaining phenyl substituents $R^3$, $R^4$, $R^5$ or $R^6$ are independently selected from the group consisting of —($C_1$–$C_7$)hydrocarbyl, —$CF_3$, —O($C_1$–$C_7$)hydrocarbyl, —O-acyl, —$NH_2$, —NH($C_1$–$C_6$)alkyl, —N(($C_1$–$C_6$)alkyl)$_2$, —NH-acyl and halogen;

* denotes a chiral carbon;

wherein the bond designated by ⁓⁓⁓ indicates that the absolute conformation about the chiral carbon may be either (R) or (S); or a pharmaceutically-acceptable salt of such a compound.

2. The method of claim 1 wherein the one phenyl substituent which is —OH is $R^3$ or $R^4$.

3. The method of claim 1 wherein one of phenyl substituents $R^3$, $R^4$, $R^5$ or $R^6$ is —OH and the remaining phenyl substituents are independently selected from the group consisting of —O($C_1$–$C_7$)hydrocarbyl; or a pharmaceutically-acceptable salt of such a compound.

4. The method of claim 3 wherein the one phenyl substituent which is —OH is $R^3$ or $R^4$.

5. The method of claim 3 wherein said remaining phenyl substituents $R^3$, $R^4$, $R^5$ or $R^6$ are independently selected from the group consisting of —O($C_1$–$C_7$)alkyl; or a pharmaceutically-acceptable salt of such a compound.

6. The method of claim 5 wherein the one phenyl substituent which is —OH is $R^3$ or $R^4$.

7. The method of claim 1 wherein one of phenyl substituents $R^3$, $R^4$, $R^5$ or $R^6$ is —OH and the remaining phenyl substituents $R^3$, $R^4$, $R^5$ or $R^6$ are —$OCH_3$; or a pharmaceutically-acceptable salt of such a compound.

8. The method of claim 7 wherein the one phenyl substituent which is —OH is $R^3$ or $R^4$.

9. The method of any one of claim 1, 3, 5 or 7 wherein $R^1$ and $R^2$ are independently selected from —($C_1$–$C_7$)alkyl; or a pharmaceutically-acceptable salt of such a compound.

10. The method of claim 9 wherein $R^1$ and $R^2$ are independently selected from —($C_1$–$C_3$)alkyl; or a pharmaceutically-acceptable salt of such a compound.

11. The method of claim 10 wherein $R^1$ is —$CH_2CH_3$ and $R^2$ is —$CH_3$; or a pharmaceutically-acceptable salt of such a compound.

12. The method of claim 1 wherein the compound of formula I is selected from the group consisting of:

1-(3,4-dimethoxyphenyl)-4-methyl-5-ethyl-7-hydroxy-8-methoxy-5H-2,3-benzodiazepine;

1-(3-hydroxy-4-methoxyphenyl)-4-methyl-5-ethyl-7,8-dimethoxy-5H-2,3-benzodiazepine;

1-(3-methoxy-4-hydroxyphenyl)-4-methyl-5-ethyl-7,8-dimethoxy-5H-2,3-benzodiazepine; and 1-(3,4-dimethoxyphenyl)-4-methyl-5-ethyl-7-methoxy-8-hydroxy-5H-2,3-benzodiazepine;

or a pharmaceutically-acceptable salt of such a compound.

13. The method of claim 12 wherein the compound of formula I is selected from the group consisting of:

1-(3-hydroxy-4-methoxyphenyl)-4-methyl-5-ethyl-7,8-dimethoxy-5H-2,3-benzodiazepine; and 1-(3-methoxy-4-hydroxyphenyl)-4-methyl-5-ethyl-7,8-dimethoxy-5H-2,3-benzodiazepine;

or a pharmaceutically-acceptable salt of such a compound.

* * * * *

UNITED STATES PATENT AND TRADEMARK OFFICE
CERTIFICATE OF CORRECTION

PATENT NO.     : 6,638,928 B1
DATED          : September 30, 2004
INVENTOR(S)    : Harris et al.

It is certified that error appears in the above-identified patent and that said Letters Patent is hereby corrected as shown below:

<u>Column 17,</u>
Lines 20, 22 and 23, change "mg/kg/day" to -- mg/day --.

Signed and Sealed this

Second Day of November, 2004

JON W. DUDAS
*Director of the United States Patent and Trademark Office*